United States Patent
Richelsoph

[19]

[11] Patent Number: 6,017,345
[45] Date of Patent: *Jan. 25, 2000

[54] SPINAL FIXATION PLATE

[75] Inventor: Marc Richelsoph, Memphis, Tenn.

[73] Assignee: Spinal Innovations, L.L.C., Bartlett, Tenn.

[*] Notice: This patent issued on a continued prosecution application filed under 37 CFR 1.53(d), and is subject to the twenty year patent term provisions of 35 U.S.C. 154(a)(2).

[21] Appl. No.: 08/854,021

[22] Filed: May 9, 1997

[51] Int. Cl.⁷ .................................................. A61B 17/82
[52] U.S. Cl. ................................ 606/70; 606/69; 606/61; 606/73
[58] Field of Search ................................ 606/61, 69, 70, 606/71, 72, 73; 623/17

[56] References Cited

U.S. PATENT DOCUMENTS

| | | | |
|---|---|---|---|
| 4,388,921 | 6/1983 | Sutter et al. . | |
| 4,493,317 | 1/1985 | Klaue | 128/92 B |
| 4,838,252 | 6/1989 | Klaue | 128/92 |
| 4,905,680 | 3/1990 | Tunc | 606/77 |
| 4,957,496 | 9/1990 | Schmidt | 606/71 |
| 5,085,660 | 2/1992 | Lin | 606/73 |
| 5,129,899 | 7/1992 | Small et al. | 606/71 |
| 5,129,903 | 7/1992 | Luhr et al. | 606/69 |
| 5,209,751 | 5/1993 | Farris et al. | 606/73 |
| 5,234,431 | 8/1993 | Keller | 606/61 |
| 5,324,290 | 6/1994 | Zdeblick et al. | 606/69 |
| 5,364,399 | 11/1994 | Lowery et al. | 606/69 |
| 5,395,371 | 3/1995 | Miller et al. | 606/72 |
| 5,520,690 | 5/1996 | Errico et al. . | |
| 5,540,690 | 7/1996 | Miller et al. | 606/72 |
| 5,545,163 | 8/1996 | Miller et al. | 606/72 |
| 5,549,612 | 8/1996 | Yapp et al. | 606/73 |
| 5,569,251 | 10/1996 | Baker et al. | 606/73 |
| 5,578,034 | 11/1996 | Estes | 606/69 |
| 5,591,166 | 1/1997 | Bernhardt et al. | 606/60 |
| 5,601,553 | 2/1997 | Trebing et al. | 606/69 |
| 5,603,713 | 2/1997 | Aust et al. | 606/69 |
| 5,607,426 | 3/1997 | Ralph et al. | 606/69 |
| 5,607,428 | 3/1997 | Lin | 606/73 |
| 5,616,142 | 4/1997 | Yuan et al. . | |
| 5,735,853 | 4/1998 | Olerud | 606/71 |

FOREIGN PATENT DOCUMENTS

| | | |
|---|---|---|
| 0 599 640 A1 | 6/1994 | European Pat. Off. . |
| 2726461 | 5/1996 | France . |
| 295 21 456 U1 | 5/1997 | Germany . |
| WO 90/12547 | 11/1990 | WIPO . |
| WO 95/35067 | 12/1995 | WIPO . |

Primary Examiner—Michael Buiz
Assistant Examiner—David O. Reip
Attorney, Agent, or Firm—Kohn & Associates

[57] ABSTRACT

A bone fixation plate assembly (10, 210, 210') for fixation of the spine includes a mechanism (26) for allowing movement between adjacent vertebrae (18) while maintaining engagement of the bone fixation plate (12, 212, 212') with the vertebrae (18).

18 Claims, 6 Drawing Sheets

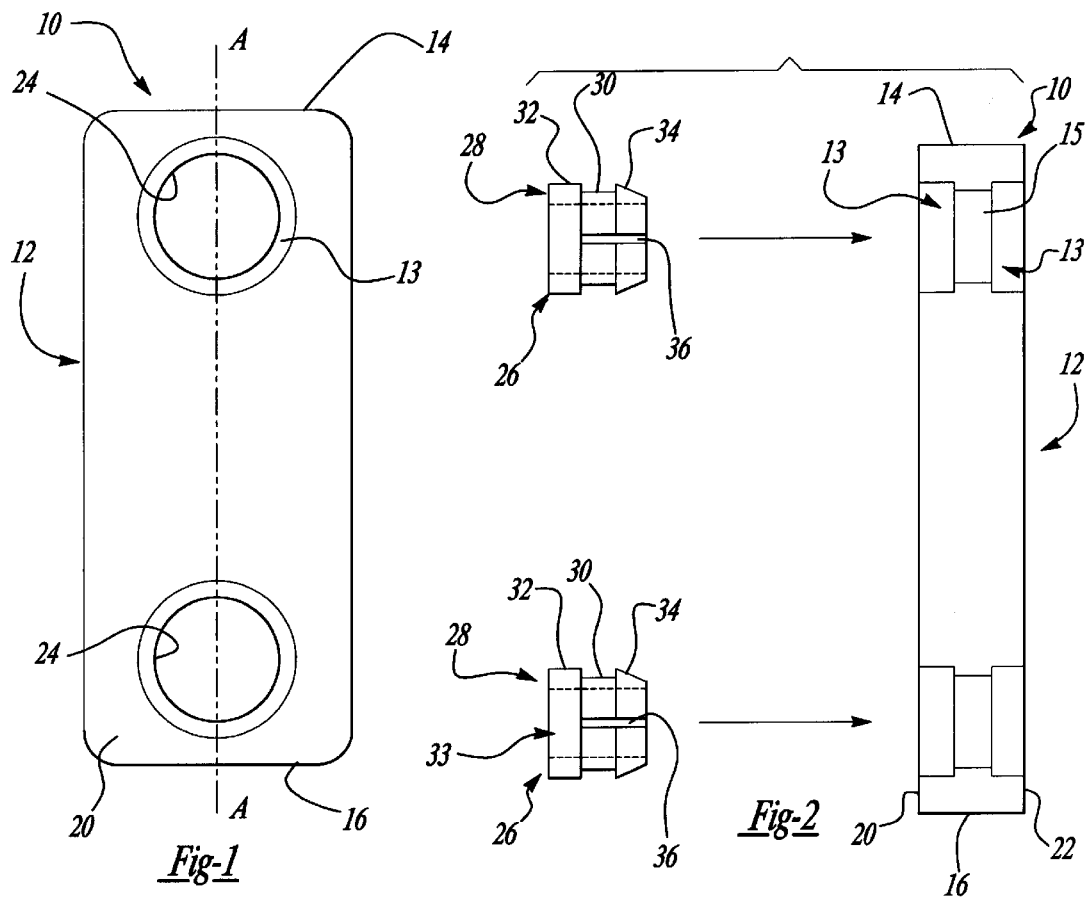
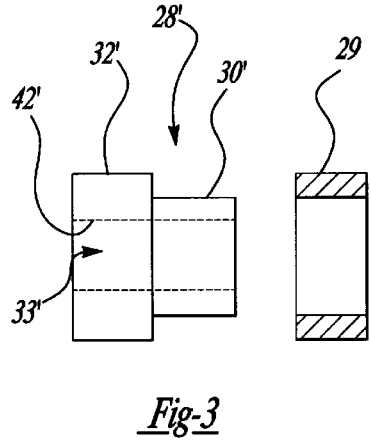
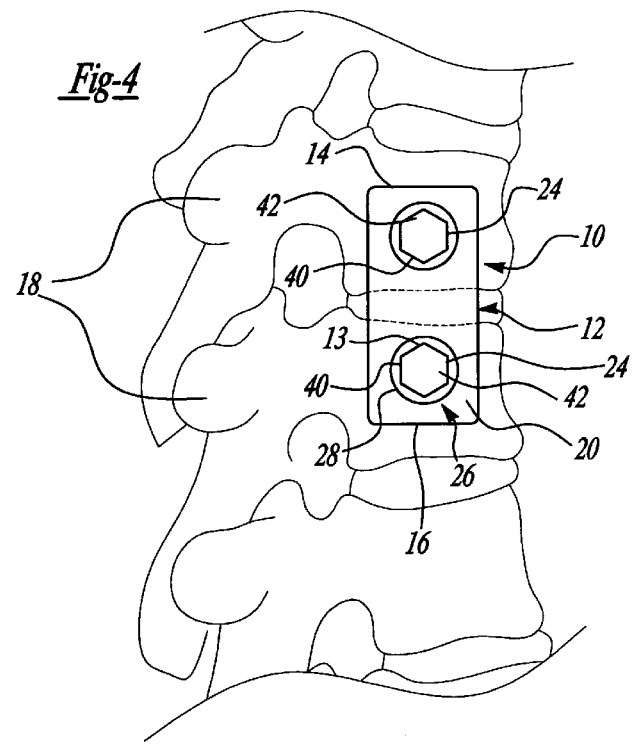

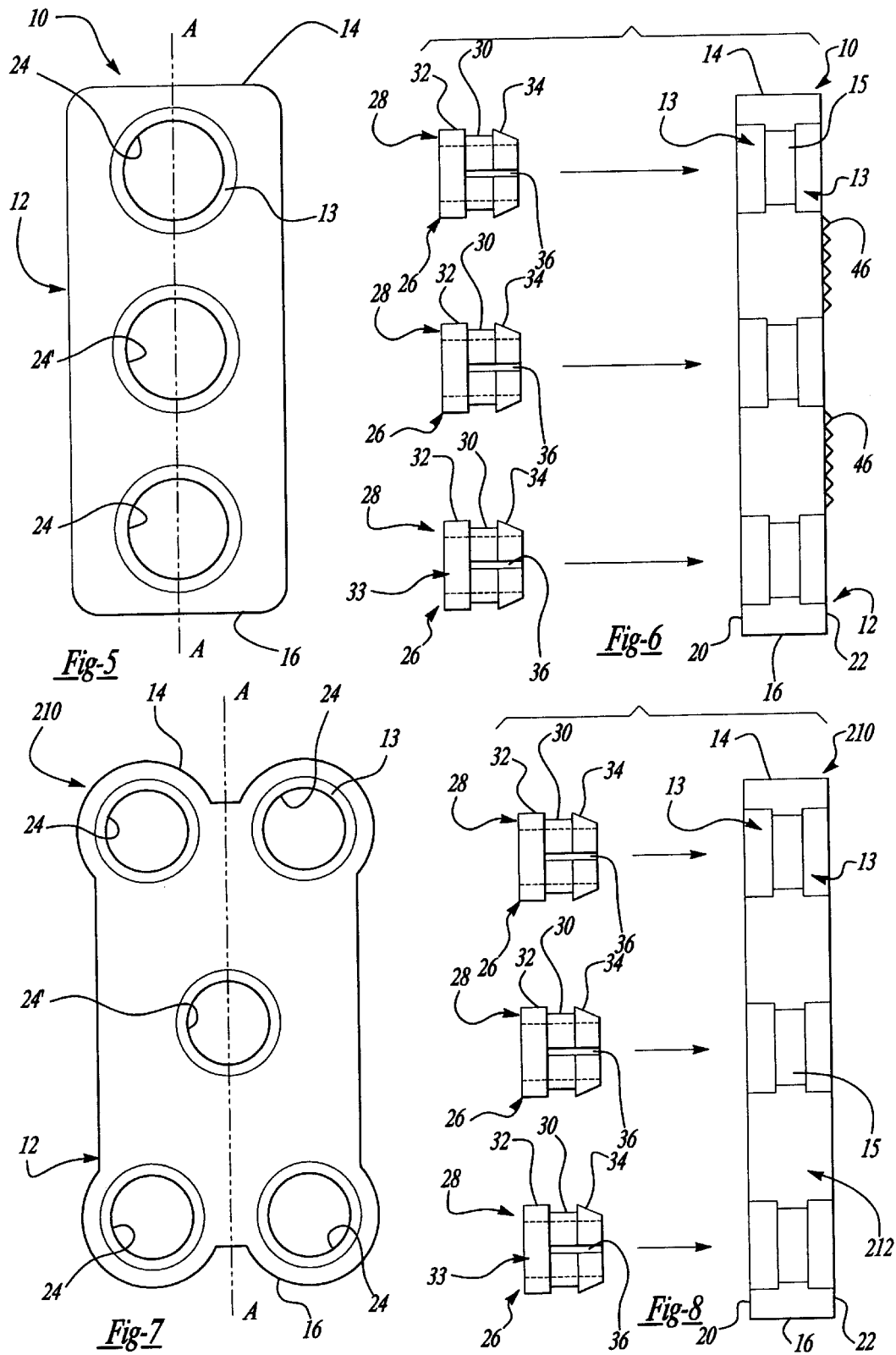

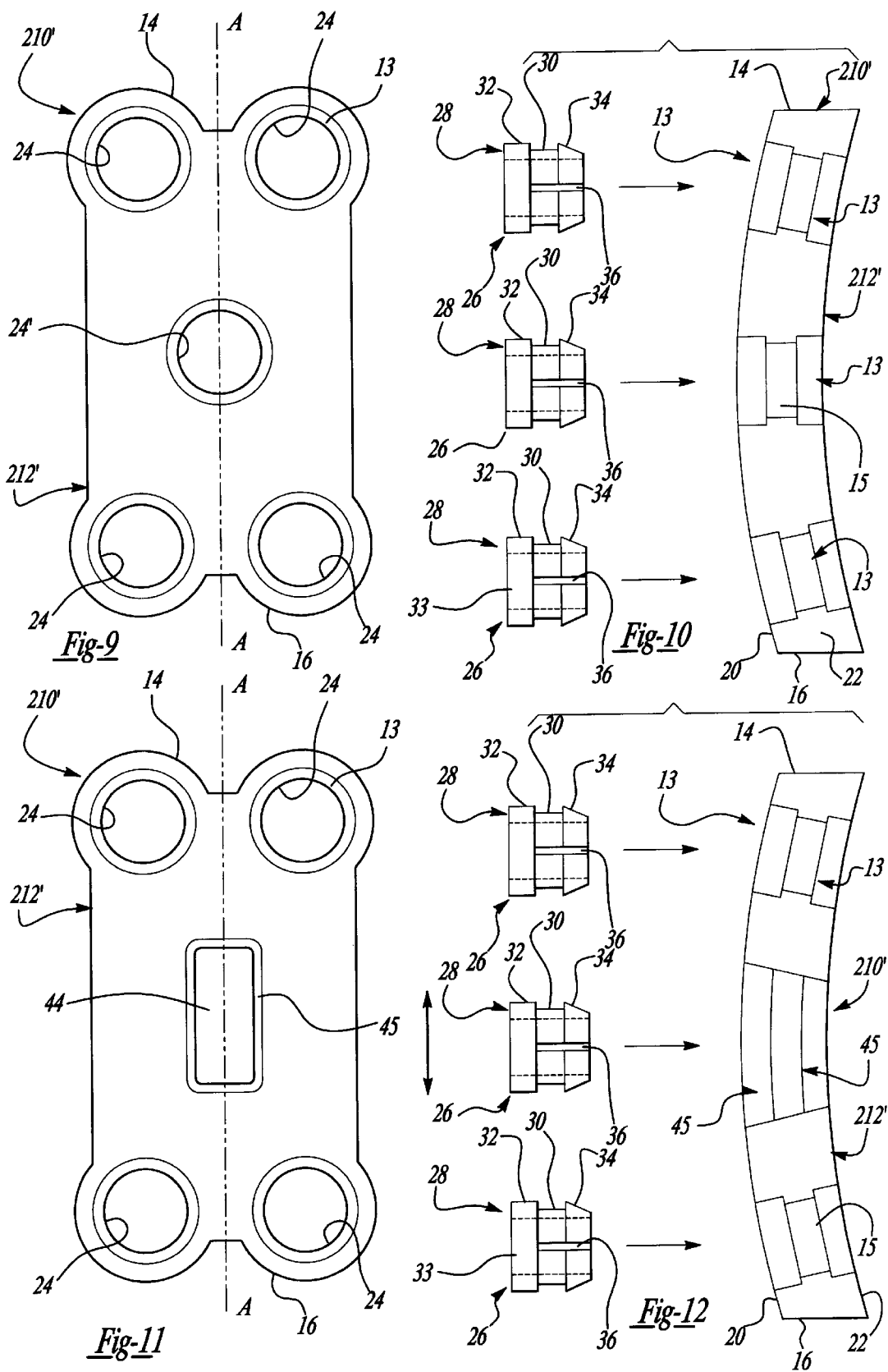

SPINAL FIXATION PLATE

TECHNICAL FIELD

The present invention relates to a bone fixation plate for anterior fixation of the spine. More particularly, the present invention prevents axial displacement of adjacent vertebrae while allowing the adjacent vertebrae to move relative to each other.

BACKGROUND OF THE INVENTION

Spinal fixation has become a common approach in treating spinal disorders, fractures, and for fusion of vertebrae. A common device used for spinal fixation is a bone fixation plate. A typical bone fixation plate includes a relatively flat, rectangular plate having a plurality of apertures therethrough. A corresponding plurality of fasteners, i.e., bone screws, are provided to secure the bone fixation plate to a bone, such as two adjacent spinal vertebrae. The screws are firmly tightened to secure the bone fixation plate to the bone or bones to be fixed. Typical examples of such bone fixation plates are illustrated in U.S. Pat. No. 5,364,399, issued Nov. 15, 1994, to Lowery et al. and U.S. Pat. No. 5,601,533, issued Feb. 11, 1997, to Trebing et al. These patents are cited as exemplary of the general state of the art with regard to bone fixation plate technology. In general, these types of devices can be utilized for anterior fixation of the spine for cervical, lumbar, and/or thoracic fixation.

The basis of anterior fixation or plating is to approach the spine from anterior or anterio-lateral approach and use the screws to solidly mount the bone fixation plate to the affected vertebrae. This approach is commonly used in cases of trauma, tumors, and degenerative conditions. Often, in addition to the application of a bone fixation plate, graft material may be combined in attempt to permanently fuse together adjacent vertebrae. The graft material can consist of bone grafts obtained from other bones in the patients body or from cadaver bones.

A common problem associated with the use of such bone fixation plates is the tendency of the bone screws to "back out" or pull away from the bone into which they were fixed. This problem occurs, primarily, due to the normal motion of the body and spine. The spine is a very dynamic entity and is constantly moving. This problem is especially prevalent in areas of high stress such as the spine. This is a particularly important problem because as the screw becomes loose and pulls away from the bone, the head of the screw can rise above the surface of the bone fixation plate and, possibly, even work its way completely out of the bone. This condition can create a number of potentially serious problems given the number and proximity of blood vessels and other critical structures near the locations of anterior spinal plate fixation.

A number of various designs have been brought forth in attempts to prevent screws from pulling away from the bone and/or to prevent the screws from backing out or pulling away from the surface of the bone fixation plate. For example, the Lowery et al. patent, discussed above, discloses an anterior cervical plating system incorporating a locking screw which engages the heads of the bone screws used to secure the cervical plate to the vertebrae. The locking screw is positioned above the bone screws and is driven against the heads of the bone screws to and rigidly fix the bone screws to the plate. However, for this locking mechanism to work, the distance between the heads of the bone screws must be kept to a minimum, thereby limiting the potential applications of the bone fixation plate. Additionally, while the Lowery et al. patent allows for the bone screws to be angled, if the screws are not angled exactly the same amount, which is very difficult to achieve, the locking screw cannot adequately contact both bone screw heads.

Another example of a mechanism for preventing bone fixation screws from backing out or becoming dislodged from the bone is set forth in the Trebing et al. patent discussed above. The Trebing et al. patent discloses a mechanism whereby the bone fixation plate is threaded and is used in combination with a bone screw having both bone engaging threads and a threaded portion near the head of the bone screw which is complimentary to the threaded hole in the bone fixation plate. In this mechanism, the screw is rigidly fixed to the bone fixation plate. However, it is possible to lock the bone screw to the bone fixation plate while leaving a gap between the bone fixation plate and the bone. This problem can cause inferior fixation of the bone or even total failure of the fixation.

Various other mechanisms used to prevent bone screws from pulling out of bones include cams which engage and lock the screws and the use of expanding head screws which expand outwardly when adequate force is applied thereto to engage the holes in the bone fixation plate. All of these particular designs have drawbacks including potential for breakage or requiring particular precision and alignment in their application in order to correctly work.

Yet another apparatus for preventing bone screw back-out from a bone fixation plate is shown in U.S. Pat. No. 5,578,034, issued Nov. 26, 1996, to Estes. The Estes patent discloses a system for internal fixation of bone which includes a bone fixation plate having a number of bores therethrough, a corresponding number of screws each having an enlarged head portion and an elongated shaft portion defining bone engaging threads thereabout and a non-threaded portion between the head and the threaded portions, and a corresponding number of screw anti-backout members each having a bore therethrough. The screw anti-backout members are inserts positioned within the bores of the fixation plate and are initially sized to slidingly receive an elongated screw shaft therethrough. During application of the fixation plate, the bone screws are advanced through the bone fixation plate bores and the screw anti-backout members which are positioned within the plate bores to screw the bone fixation plate to the underlying bone. Thereafter, the apparatus is sufficiently heated to shrink the bores of the screw anti-backout members, thereby trapping the non-threaded portion of the screw shafts located between the fixation plate and the threaded portions. The anti-backout collars are immobilized within the bore of the fixation plate. Thus, the collar and fixation plate remain in fixed relationship to each other after fixation to the underlying bone.

Other types of inserts or collars have been used with bone fixation plates for a variety of reasons such as those shown in U.S. Pat. No. 4,388,921, issued Jun. 21, 1983, to Sutter et al. and U.S. Pat. No. 5,607,428, issued Mar. 4, 1997, to Lin. Sutter et al. discloses a bone fixation plate in which sleeves are placed in openings provided in a bone fixation plate. A screw is placed through the sleeve and into the underlying bone. By tightening the screw, the sleeve is clamped in place with relation to the bone fixation plate thus assuring that the fixation plate will stay rigidly connected with the screws.

The Lin patent discloses a bone fixation plate having a direction adjusting ring disposed in at least one hole in the fixation plate. Upon insertion and tightening of the threaded bone screw, arresting edges of the direction adjusting ring are urged into engagement within the hole to securely fix and retain the direction adjusting ring therein.

Both the Sutter et al. and Lin patents disclose, similar to those patents described above, an insert that is rigidly disposed or fixed in a hole or aperture in the fixation plate. They do not allow for movement of the insert with relation to the bone fixation plate.

Therefore, it would be desirable to provide a bone fixation assembly which would allow positive, rigid fixation of a bone fixation plate to a bone, such as adjacent vertebrae, while allowing movement, stress, or dynamic load sharing of the adjacent vertebrae thereby enhancing the bone rebuilding process and enhancing the success of a bone graft. Additionally, it would be desirable to have a bone fixation plate assembly which would prevent the application of high stress on the screws and plate which would lead to failure of the assembly, including the actual breakage of the screws and closure of the previously formed gap between the adjacent vertebrae. Additionally, it would also be desirable to provide a bone fixation plate assembly that allows the fixation screws to be locked to the plate to prevent the screws from backing out of the plate while allowing the plate to be firmly seated against the underlying bone. Further, it would desirable to provide a bone fixation plate assembly which requires no small parts nor requires no additional steps to lock the screws to the bone fixation plate.

SUMMARY OF THE INVENTION

In accordance with the present invention, a bone fixation plate assembly for fixation of the spine includes a mechanism for allowing movement between adjacent vertebrae while maintaining engagement of the bone fixation plate with the vertebrae.

BRIEF DESCRIPTION OF THE DRAWINGS

Other advantages of the present invention will be readily appreciated as the same becomes better understood by reference to the following detailed description when considered in connection with the accompanying drawings wherein:

FIG. 1 is a top view of a bone fixation plate in accordance with the present invention;

FIG. 2 is an exploded side view, partially in cross-section, of a bone fixation plate in accordance with the present invention;

FIG. 3 is an exploded side view, partially in cross-section, of an alternative embodiment of an insert in accordance with the present invention;

FIG. 4 is a representation of an upper cervical spine having a bone fixation plate assembly in accordance with one embodiment of the present invention affixed thereto;

FIG. 5 is a top view of another embodiment of the bone fixation plate in accordance with the present invention;

FIG. 6 is an exploded side view, partially in cross-section, of an embodiment of the bone fixation plate assembly shown in FIG. 5;

FIG. 7 is a top view of another embodiment of the bone fixation plate in accordance with the present invention;

FIG. 8 is an exploded side view of the embodiment of the bone fixation plate shown in FIG. 7;

FIG. 9 is a top view of another embodiment of the bone fixation plate in accordance with the present invention;

FIG. 10 is an exploded side view of the embodiment of the bone fixation plate shown in FIG. 9;

FIG. 11 is a top view of another embodiment of the bone fixation plate in accordance with the present invention;

FIG. 12 is an exploded side view of the embodiment of the bone fixation plate shown in FIG. 11;

DETAILED DESCRIPTION OF THE INVENTION

Figure 13:
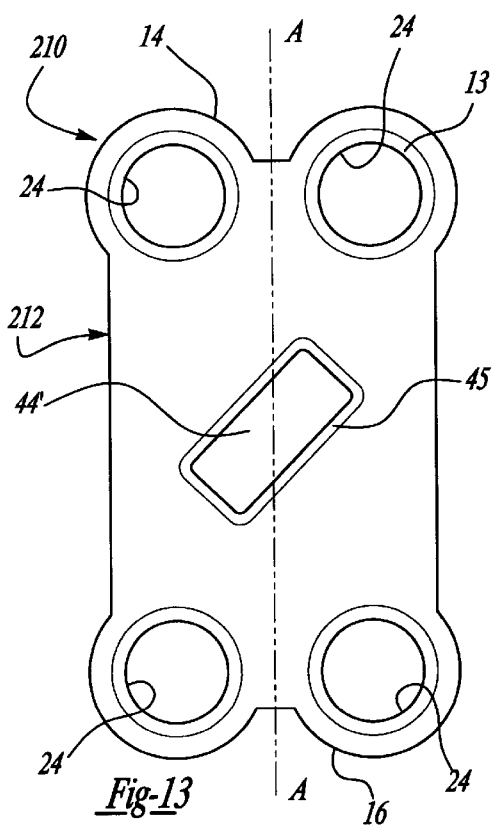
FIG. 13 is a top view of another embodiment of the bone fixation plate in accordance with the present invention.

A bone fixation plate assembly constructed in accordance with the present invention is generally shown at 10 in FIG. 1 and in an exploded view in FIG. 2.

More generally, referring additionally to FIG. 4, the bone fixation plate assembly 10 includes a substantially flat elongated bone fixation plate 12 having a longitudinal axis (A) defined by a first end 14 and a second end 16. The length of the elongated bone fixation plate along the axis (A) should be sufficient enough to span between adjacent vertebrae 18. The elongated bone fixation plate 12 also includes an upper surface 20 and a lower surface 22. the lower surface 22 is adapted to engage the vertebrae 18.

Apertures 24 can be disposed at each end 14,16 of the bone fixation plate 12. A mechanism 26 for allowing movement between adjacent vertebrae 18 while maintaining engagement of the bone fixation plate 12 with the vertebrae 18 is disposed in the bone fixation plate assembly 10.

More specifically, referring to FIGS. 2 and 4, the mechanism 26 for allowing movement between the adjacent vertebrae 18 includes an insert 28 disposed in at least one of the apertures 24 for receiving an retaining a screw 40 therein. The insert 28 is rotatably fixed within the aperture 24 and can freely rotate therein. When the screw is inserted and tightened within the insert 28, both the screw 40 and the insert 28 can rotate axially about the longitudinal axis of the screw 40 while simultaneously preventing axial movement of the screw 40 with relation to the bone fixation plate 12.

Additionally, the insert 28 can be fixed within the aperture 24 with a degree of side to side play between the insert 28 and the bone fixation plate 12 such that not only can the insert 28 rotate freely within the aperture 28, the insert 28 can move from side to side or wobble within the aperture 24. By wobbling or rocking within the aperture 24, the insert 28 allows for longitudinal movement of the underlying bones with respect to the screws 40 to be tolerated and absorbed by the bone fixation assembly 10. That is great movement and shifting of the underlying bones to which the assembly 10 is affixed to can be acceptably tolerated without failure of the assembly 10 or damage to surrounding tissues or structures.

The ability of the insert 28 to rotate and/or wobble within the bone fixation plate is important as it is well understood according to Wolff s Law that bones grow along lines of stress. Therefore, in order for fusion to occur between two or more vertebral bodies, a graft placed between the vertebral bodies must be loaded or stressed for solid bone fusion to occur. The biology of bones makes the fusion process very dynamic. Graft material slowly resorbs as osteoclasts remove bone and osteoblasts replace bone with new living bone. With a rigid plate construct, where the screws hold the vertebral bodies at a fixed apart distance, any resorption of the bone graft reduces or eliminates the compression or stress forces on the graft. Accordingly, these rigid plate constructs can induce or cause a condition known as psuedoarthrosis. Therefore, in accordance with the present invention, it is important to maintain the graft under load and/or stress while allowing the plate to compensate for the bone dynamics. This can be accomplished utilizing the mechanism 26 as described herein.

The insert 28 is mounted within the aperture 24. Preferably, the aperture 24 is a circular bore. The bore can include at least one internal annular recess 13 disposed in either the upper surface 20, the lower surface 22, or both surfaces of the bone fixation plate 12 and a passageway 15 therebetween defined by the bore of the aperture 24. The, insert 28 is in mating engagement with the internal annular recess or recesses 13 to lock the insert 28 within the bone fixation plate 12.

The insert 28 includes a locking mechanism 42 for locking the screw 40 within the bone fixation plate 12. Preferably, the locking mechanism 42 includes threads disposed within an axial bore 33 which are adapted engage and retain the screw 40 therein. Referring to FIG. 2, the insert includes an annular recess 30 defined at one end by a circumferential threaded screw receiving flange 32 and at the other end by a frustoconical or wedge-shaped insert flange 34. The axial bore 33 extends from the circumferential threaded screw receiving flange 32 to the end of the frustoconical insert flange 34. The annular recess 30 and the frustoconical insert portion 34 can be biased outwardly and can include a transverse slot 36 disposed therein which bisects both the annular recess 30 and the insert flange 34.

During insertion of the insert 28 within the aperture 24, both the frustoconical insert portion 34 and the annular recess 30 are compressed as the frustoconical insert portion 34 engages the walls of the annular internal recess 13 of the bone fixation plate 12. That is, the frustoconical shape of the insert portion 34 acts as a ramping surface which, when in contact with the annular internal recess 13, gradually compresses the insert portion 34 and the annular recess 30 by compressing or closing the transverse slot 36. When the insert portion 34 and annular recess 30 are compressed, they are able to pass through the channel 15 of the aperture 24 until they reach the internal recess disposed in the lower surface 22 of the bone fixation plate or side opposite which the insert 28 was inserted. Once the frustoconical insert portion 34 exits from the channel 15 of the aperture 24, the outward biasing force causes the frustoconical insert portion 34 to expand and engage the walls of the internal recess 13 to lock the insert 28 within the bone fixation plate 12. Since the diameter of the uncompressed frustoconical insert portion 34 is larger than the diameter of the bore of the aperture 24, the frustoconical or wedge shaped portion of the insert 24 prevents the withdrawal of the insert 28 from the aperture 24. Thus, the insert 28 is locked into the bone fixation plate 12.

The diameter of the annular recess 30 can also be smaller than the diameter of the bore or aperture 24 so that the insert 28 is free to rotate within the aperture 24.

Alternatively, an insert 28' can be constructed in multiple parts as shown in FIG. 3. The insert 28' can include an axial bore 33' having threads 42' disposed therein. The insert 28' also can include a circumferential threaded screw receiving portion 32' and an annular recess 30'. A retaining member 29 which includes structure for engaging a portion of the annular recess 30' can be provided to retain the insert 28' within the recess 13 of the bone fixation plate 12. The retaining member 29 can be affixed to the annular recess 30' by means such as compression fitting, threaded engagement, or by other means well known to those skilled in the art.

Referring to FIG. 4, a bone fixation plate assembly 10 is shown affixed to two adjacent vertebrae 18. The bone fixation plate 12 is mounted to the adjacent vertebrae 18 by way of a number of bone engaging screws 40. The screw 40 is in threaded engagement with the insert 28 as is shown in phantom at 42.

Numerous embodiments of the invention are contemplated. For example, referring to FIGS. 5 and 6, a bone fixation assembly designated as 10 is shown. In this embodiment, the bone fixation plate 12 is substantially flat and includes two apertures 24 disposed at the end 14,16 of the bone fixation plate 12 and also includes at least one additional aperture to 24' disposed between the ends 14,16 of the bone fixation plate 12. In this embodiment, the aperture 24' disposed between the ends 14,16 of the bone fixation plate 12 is equidistantly disposed between the ends 14,16 of the bone fixation plate 12 along the longitudinal axis (A). However, the aperture 24' disposed between the ends 14,16 of the bone fixation plate 12 can be disposed at any point in between the ends 14,16 of the bone fixation plate 12. Additionally, the additional aperture 24' can be disposed adjacent to the longitudinal axis (A). The placement of the additional apertures 24' depends upon the application to which the assembly 10 is to be applied.

Referring to FIGS. 7 and 8, an additional embodiment of a substantially flat bone fixation plate assembly 10 is provided wherein five apertures 24, 24' are utilized. In this embodiment, two apertures 24 are disposed at each end 14,16 of the bone fixation plate 12. An additional aperture 24' is equidistantly disposed between the ends 14,16 and along the longitudinal access (A) of the bone fixation plate 12.

As shown in FIGS. 9 and 10, a further embodiment of the assembly is shown. This embodiment is similar to the embodiment shown in FIGS. 7 and 8, however, the bone fixation plate assembly is arcuately shaped or curved transverse to the longitudinal access (A) to conform the bone fixation plate 212' to the curvature of the vertebrae. Utilization of a curved or formed fixation plate 12', 212' can be incorporated into any embodiment of the bone fixation assembly in accordance with the present invention and is not limited by the specific embodiments disclosed herein which are provided as examples of the possible designs which can be utilized with the present invention.

Referring to FIGS. 11 and 12, a further embodiment of the bone fixation plate assembly of the present invention is shown at 210'. This embodiment includes a curved, elongated, a substantially bone fixation plate 212' including rectangular slot 44 having a recess 45 disposed therein. The elongated slot 44 is disposed substantially parallel to the longitudinal axis (A) of the bone fixation plate 212".

The substantially rectangular slot 44 allows the insert 28 to be adjustably positioned at various locations within the slot 44. By being adjustable, the assembly 210' is able to be utilized in a greater number of locations and applications.

Additionally, the insert 28 disposed in the slot 44 can be allowed to slide freely within the slot 44 to accommodate movement of the underlying bone or bones.

Figure 14:
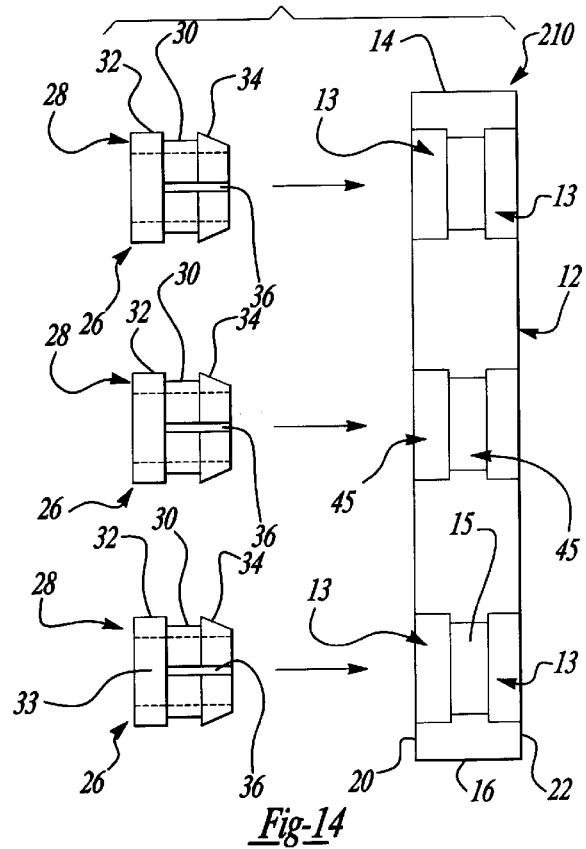
FIG. 14 is an exploded side view of the embodiment of the bone fixation plate shown in FIG. 13.

Referring to FIGS. 13 and 14, a further embodiment 210 is shown having as an elongated slot 44'. The elongated slot 44' is disposed at a substantially acute angle with respect to the longitudinal axis (A) of the substantially flat bone fixation plate 212.

Figure 15:
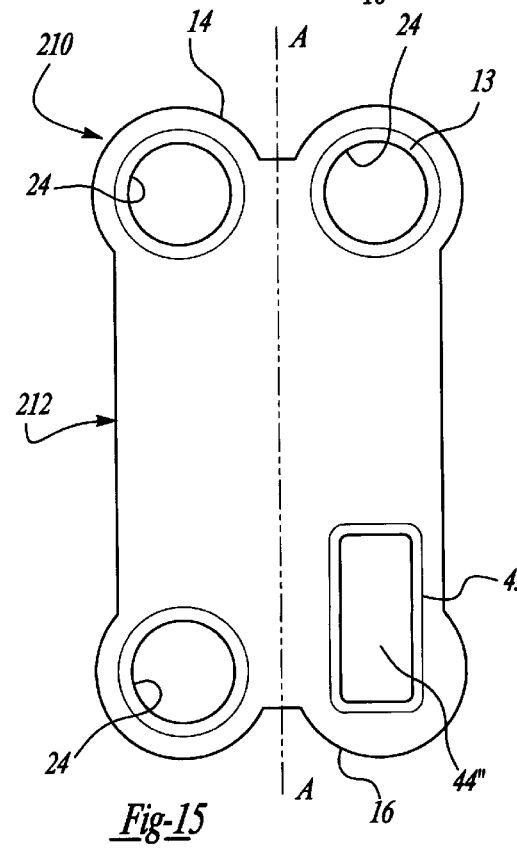
FIG. 15 is a top view of another embodiment of the bone fixation plate in accordance with the present invention.

In a further embodiment shown in FIG. 15, an elongated slot 44" is shown disposed at one end 16 of the bone fixation plate 212 and parallel to the longitudinal axis (A).

In all of the embodiments shown in FIGS. 11 through 15, the elongated slot 44, 44', 44" accepts at least one insert 28, 28' therein. The inserts 28, 28' can be affixed within the recess 45 in a manner similar to that discussed above. The elongated slot 44, 44', 44" allows for a substantial margin for adjustment and proper location of the screw 40 and the bone fixation plate 12, 212, 212' and, as discussed above, the inserts 28, 28' can be made to slide freely within the slot 44, 44', 44".

The spacing or orientation of the apertures 24, 24', the slots 44, 44', 44", and the inserts 28, 28' within the bone fixation plate assembly 10, 210, 210' can be designed and selected so as to achieve a desired dynamic load sharing arrangement between the screws 40 disposed in the various combinations of apertures 24, 24' and slots 44, 44', 44" described above. That is, the bone fixation plate assembly 10, 210, 210' can be tailored to a specific application such that the load carried by each screw 40 can be distributed in a desired manner, including load shifting after the assembly 10, 210, 210' has been affixed to the underlying bone. Thus, the assembly 10, 210, 210' can accommodate the dynamic environment into which it is utilized without incurring the drawbacks of the prior art devices described above.

Referring to FIG. 6, the bone fixation assembly 10 is shown including a bone engagement mechanism 46 disposed on the lower surface 22 of the bone fixation plate 12 for enhancing the engagement of the bone fixation plate 12 to the vertebrae. Preferably, the bone engagement mechanism 46 includes a texturized surface disposed on substantially all of the lower surface 22 of the bone fixation plate 12. In other embodiments, the texturized surface can be disposed on only a portion of the lower surface 22 as is shown in FIG. 6.

The texturized surface can include etched, roughened, grooved, knurled, or like contouring of the lower surface 22 of the bone fixation plate 12 as is well known in the art.

Figure 16:
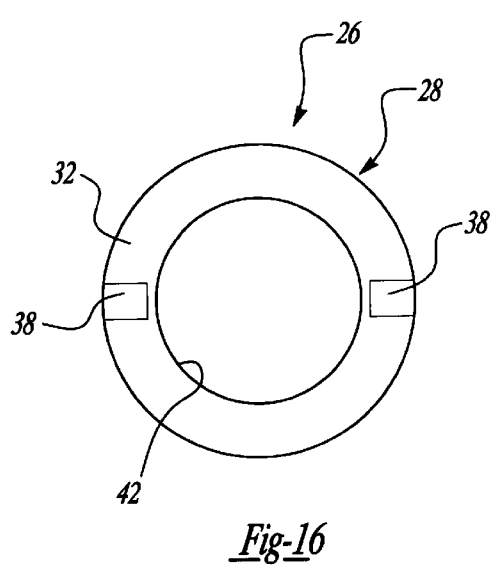
FIG. 16 is a top view of an insert in accordance with the present invention.

Referring to FIG. 16, the screw receiving portion 32 of the insert 28 is shown in greater detail. At least two rectangular recesses 38 are disposed therein. The recesses 38 are adapted to receive a device, such as a screwdriver or similar tool, to prevent rotation of the insert 28 within the aperture 24 during the insertion and tightening of the screw 40 disposed therein to the underlying bone. The location and configuration of the recesses 38 within the screw receiving portion 32 of the insert 28 can be varied according to a desired or specific tool to be utilized for the purpose of preventing rotation of the insert means 28. In operation, the tool or device would be placed in mating engagement with the recesses 38 thereby providing leverage to withstand the rotational or torque forces applied to the insert 28 via the threads 42 disposed in the bore 33 of the insert 28 as transmitted thereto by the screw 40.

Figure 17:
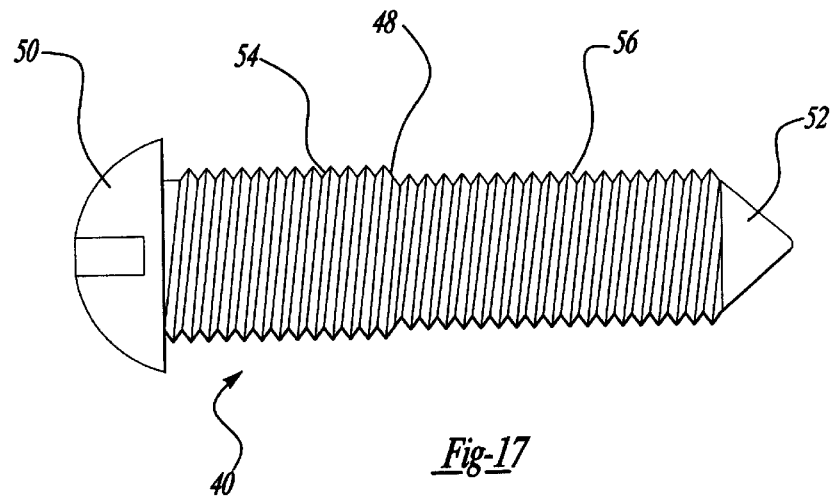
FIG. 17 is a side view of a bone screw utilized with the bone fixation assembly of the present invention.

The screws 40 utilized for securing the bone fixation plate assembly 10, 210, 210' to underlying bone are generally bone screws of the type well known in the art. Preferably, the screws 40 utilized in the present invention are of the type illustrated in FIG. 17. The screw 40 typically comprises a screw with a shaft having a head 50 and a tip 52. The shaft 48 is threaded and includes two differently threaded portions 54, 56. Portion 54 is threaded to threadingly engage with the threads 42 of the insert 28. The threaded portion 56 is threaded to specifically engage bone. An example of a screw which can be used with the bone fixation plate assembly 10, 210, 210' of the present invention is shown in U.S. Pat. No. 5,601,553 to Trebing et al., and is incorporated herein by, reference. Alternatively, the screw threads 54, 56 can utilize the same thread for both portions.

Figure 18:
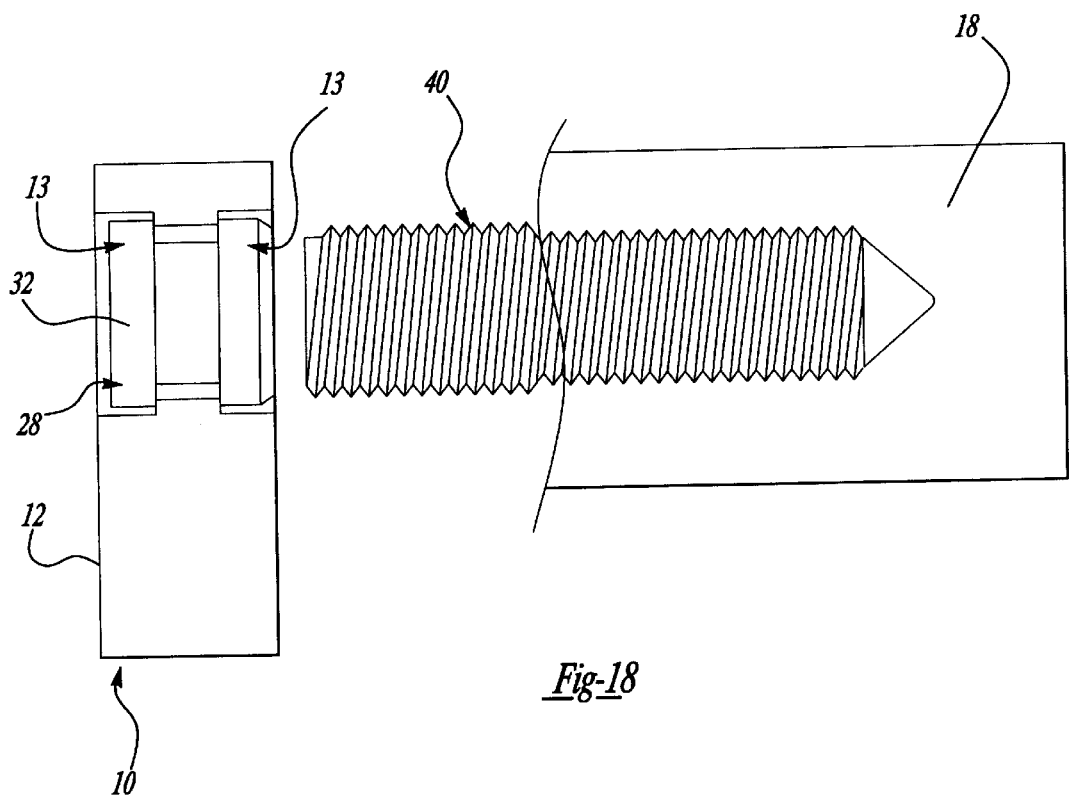
FIG. 18 is an exploded side view, partially in cross-section, of an alternative mechanism of fixation in accordance with the present invention.

In an alternative mechanism for fixation of the bone fixation plate assembly 10 to the vertebrae 18 as shown in FIG. 18, a headless screw 40 can first be driven into and affixed within the bone. The bone fixation plate 12, 212, 212' of the bone fixation assembly 10, 210, 210' having an insert 28, 28' disposed therein would then be disposed over the portion of the screw 40 protruding from the bone and would be fixed to the bone fixation plate 12, 212, 212' and insert 28 by threadingly engaging the threaded screw receiving portion 32 of the insert 28, 28' with the threads of the portion of the screw 40 protruding from the bone.

Figure 19:
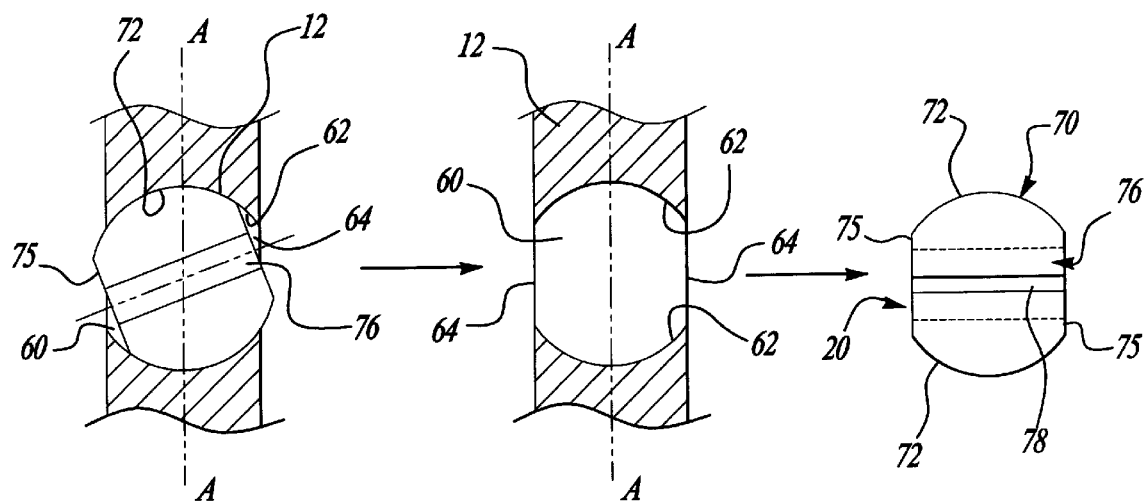
FIG. 19 is an exploded side view, partially in cross-section and fragmented, of an alternative insert in accordance with the present invention.
Figure 20:
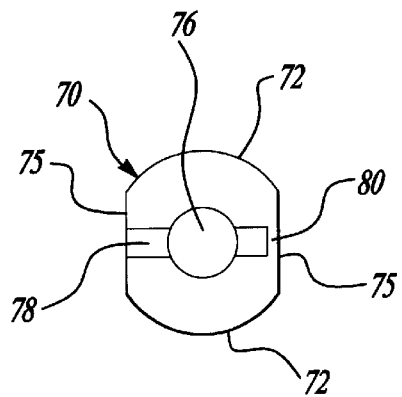
FIG. 20 is an end on view of an alternative insert in accordance with the present invention taken along lines 20—20 of FIG. 19.

Referring to FIGS. 19 and 20, an alternative embodiment for both an alternative insert 70 and aperture 60 is shown. The aperture 60 which can be disposed in any plate 12, 212, 212' includes, in cross-section, substantially arcuate ends 62 and substantially straight sides 64 which can be machined into the bone fixation plate 12, 212, 212'. The ends 62 are substantially hemispherical and matingly engage within the aperture 60. Into the aperture 60, an insert 70 including substantially hemispherical portions 72 disposed at the ends of the insert 70 and substantially straight side portions 75 can be disposed. An axial threaded bore 76 in the insert 70 is provided to accept bone screws 40 therein. A transverse slot 78 is provided in the insert 70 to allow the insert 70 to be contracted or to be compressed to facilitate its insertion within the aperture 60.

Referring specifically to FIG. 20, the biasing mechanism of the insert 70 is shown in greater detail. The transverse slot 78 extends through the insert 70 substantially bisecting the insert 70. A portion 80 of the insert 70 defines a terminal margin of the slot 78. This portion 80 of the insert 70 allows the insert 70 to be compressed for insertion into the aperture 60. That is, the portion 80 acts as a hinge or spring to allow the insert 70 to compress and to expand. The insert 70 can be biased outwardly as described above for the insert 28. After insert 70 is disposed within the aperture 60, the insert 70 freely rotates within the bore 76 and also, the insert 70 can be moved or positioned to any angle such that the bore 76 is angled with respect to the axis (A) of the plate 12, 212, 212'. The ability of the insert 70 to be angled with respect to the longitudinal axis (A) of the plate 12, 212, 212' allows for the screws 40 to be inserted at angles with respect to the longitudinal axis (A) of the plate 12, 212, 212'.

The advantage of the insert 70 being able to rotate in more than one plane is that it allows a surgeon to place the screw at any angle in necessary order to adapt the bone fixation assembly 10, 210, 210' for varying anatomy. Therefore, a surgeon could place the screws such that they are convergent or divergent and facing in the caudal or cephalad directions. Thus, in cases of severe deformity, the multi-angle positionable insert 70 would allow easier correction of the deformity while still allowing for the utilization of the low profile plate 12, 212, 212'.

The bone fixation plate assembly 10, 210, 210' of the present invention can be constructed of any suitable material. Preferably, the assembly 10, 210, 210' and other components, such as the inserts 28, 28', and 70, are constructed of suitable materials which are compatible with the uses and environments into which the assembly 10, 210, 210' will be utilized. Preferably, the assembly 10, 210, 210' is constructed of metallic materials such a titanium, stainless steel, or other metal alloys. The material which the assembly 10, 210, 210' is constructed of should have strength and be non-reactive and non-antigenic to biological systems.

Throughout this application, various publication are referenced by citation and number. Full citations for the publication are listed below. the disclosure of these publications in their entireties are hereby incorporated by reference into this application in order to more fully describe the state of the art to which this invention pertains.

The invention has been described in an illustrative manner, and it is to be understood the terminology used is intended to be in the nature of the description rather than of limitation.

Obviously, many modifications and variations of the present invention are possible in light of the above teachings. Therefore, it is to be understood that within the scope of the appended claims, reference numerals are numerals are merely for convenience and are not to be in any way limiting, the invention may be practiced otherwise than as specifically described.

What is claimed is:

1. A bone fixation plate assembly (10, 210, 210') for fixation of adjacent vertebrae of the spine comprising:
   a fixation plate (12, 212, 212') including first and second ends (14, 16) and at least one aperture (24, 24', 60) disposed at each of said first and second ends (14, 16) thereof;
   at least one bone screw (40); and
   locking means (26) for allowing movement between the adjacent vertebrae while simultaneously maintaining engagement of said bone fixation plate (12) against the vertebrae, said locking means (26) including an insert (28, 28', 70) loosely retained within at least one of the apertures (24, 24', 60) for receiving and retaining the screw (40) therein, said insert comprising a threaded axial throughbore (33);
   wherein a threaded portion (54) of the screw is configured to engage the threaded axial throughbore (33) of the insert and provide a locked condition wherein the screw is prevented for moving relative to said insert and is in non-engagement with said plate, and wherein the screw (40) and insert (26) form an assembly which is loosely retained to the plate so as to allow movement of the assembly in all directions relative to said plate (12, 212, 212').

2. A bone fixation plate assembly (10, 210, 210') according to claim 1, wherein said bone fixation plate (12, 212, 212') includes a longitudinal axis (A) defined by a first end (14) and a second end (16) and a length along said axis (A) sufficient to span between the adjacent vertebrae (18), said bone fixation plate (12, 212, 212') including an upper (20) and a lower (22) surface, said lower surface (22) adapted to engage the vertebrae (18).

3. A bone fixation plate assembly (10, 210, 210') according to claim 2, wherein said at least one aperture (24, 24') is a bore.

4. A bone fixation plate assembly (10, 210, 210') according to claim 3, wherein said bore includes at least one internal recess (13) disposed in at least one of said upper and lower surfaces of said plate.

5. A bone fixation plate assembly (10, 210, 210') according to claim 4, wherein said insert means (28, 28') is in mating engagement with said internal recess (13) to lock said insert means (28, 28') within said bone fixation plate (12, 212, 212').

6. A bone fixation plate assembly (10, 210, 210') according to claim 2, wherein said bone fixation plate (12, 212, 212') includes at least one aperture (24') disposed between said ends (14,16) of said bone fixation plate (12, 212, 212').

7. A bone fixation plate assembly (10, 210, 210') according to claim 6, wherein said at least one aperture (24') disposed between the ends (14,16) of said bone fixation plate (12, 212, 212') is disposed along the longitudinal axis (A) of said bone fixation plate (12, 212, 212').

8. A bone fixation plate assembly (10, 210, 210') according to claim 2, wherein said lower surface (22) includes bone engagement means (46) for enhancing the engagement of said bone fixation plate (12, 212, 212') to the vertebrae (18).

9. A bone fixation plate assembly (10, 210, 210') according to claim 8, wherein said bone engagement means (46) includes a texturized surface disposed on substantially all of said lower surface (22) of said bone fixation plate (12, 212, 212').

10. A bone fixation plate assembly (10, 210, 210') according to claim 9, wherein said texturized surface is disposed on a portion of said lower surface (22).

11. A bone fixation plate assembly (10, 210, 210') according to claim 1, wherein said insert means (28, 28', 70) freely rotates within said aperture (24, 24', 60).

12. A bone fixation plate assembly (10, 210, 210') according to claim 1, wherein said at least one aperture (24,24') includes at least one elongated slot (44,44', 44") having a recess (45) disposed in said bone fixation plate (12, 212, 212').

13. A bone fixation plate assembly (10, 210, 210') according to claim 12, wherein said elongated slot (44, 44") is disposed substantially parallel to the longitudinal axis (A) of said bone fixation plate (12, 212, 212').

14. A bone fixation plate assembly (10) according to claim 13, wherein said elongated slot (44, 44") is disposed at one end (14,16) of said bone fixation plate (12, 212, 212').

15. A bone fixation plate assembly (10, 210, 210') according to claim 12, wherein said elongated slot (44') is disposed at a substantially acute angle with respect to said longitudinal axis (A) of said bone fixation plate (12, 212, 212').

16. A bone fixation plate assembly (10, 210, 210') according to claim 1, wherein said bone fixation plate (12, 212, 212') is curved transverse to said longitudinal axis (A) to conform said bone fixation plate (12, 212, 212') to the curvature of the vertebrae (18).

17. A bone fixation plate assembly (10, 210, 210') according to claim 1, wherein said insert means (28) includes an annular recess (30) defined at one end by an circumferential threaded screw receiving portion (32) and at the other by a frustoconical insert portion (34), said annular recess (30) and said frustoconical insert portion (34) being biased outwardly and include a transverse slot (36) disposed therein whereby upon insertion of said insert means (28) into said aperture (24, 24'), said annular recess (30) and said frustoconical insert portion (34) deflect inwardly to allow said annular recess (30) and said frustoconical insert portion (34) to pass through said bone fixation plate (12, 212, 212') and then deflect outwardly to lock said insert means (28) into said bone fixation plate (12, 212, 212').

18. A bone fixation plate assembly (10, 210, 210') according to claim 1, wherein said screw receiving portion (32) of said insert means (28) includes at least two recesses (38) adapted to receive a device to prevent rotation of said insert means (28) within said aperture (24,24') during insertion and tightening of the screw (40) disposed therein.

* * * * *